United States Patent

Miglio et al.

[11] Patent Number: 5,600,054
[45] Date of Patent: Feb. 4, 1997

[54] PROCESS FOR THE SKELETON ISOMERIZATION OF LINEAR OLEFINS

[75] Inventors: Roberta Miglio, Trecate; Ugo Cornaro, Seriate, both of Italy

[73] Assignee: Snamprogetti S.p.A., Milan, Italy

[21] Appl. No.: 381,062

[22] Filed: Jan. 31, 1995

[30] Foreign Application Priority Data

Feb. 11, 1994 [IT] Italy .................... MI94A0243

[51] Int. Cl.$^6$ .................................................. C07C 5/27
[52] U.S. Cl. .................................... 585/671; 585/500
[58] Field of Search .......................... 585/500, 671

[56] References Cited

U.S. PATENT DOCUMENTS 2,407,918  9/1946  Burgin .
2,422,884  6/1947  Burgin .
5,227,569  7/1993  O'Young .

FOREIGN PATENT DOCUMENTS 2561945  10/1985  France .
2120205  11/1972  Germany .

*Primary Examiner*—Glenn A. Caldarola
*Assistant Examiner*—E. D. Irzinski
*Attorney, Agent, or Firm*—Oblon, Spivak, McClelland, Maier & Neustadt, P.C.

[57] ABSTRACT

Process for the skeleton isomerization of linear olefins, preferably n-butenes or n-pentenes, which consists in putting said olefins in contact with a catalyst comprising alumina on whose surface boron oxide is deposited in a quantity which is lower than $2.1 \times 10^{-4}$ g/m$^2$ of the surface of the alumina.

9 Claims, 1 Drawing Sheet

PROCESS FOR THE SKELETON ISOMERIZATION OF LINEAR OLEFINS

BACKGROUND OF THE INVENTION

1. Field of the Invention

The present invention relates to a process for the skeleton isomerization of n-butenes and n-pentenes.

2. Discussion of the Background

The necessity of converting olefins with a linear chain into branched olefins, especially with respect to C4 olefins, is a consequence of the reformulation of benzenes in progress during the last few years. The most recent regulation includes the introduction of a minimum quantity of oxygen. The compound containing oxygen which has proved so far to be the most suitable for this purpose is methylterbutylether (MTBE), which is produced on an industrial scale from methanol and iso-butene. At present the restricting factor in the production of MTBE is the availability of the branched olefin. Processes of skeleton isomerization which allow C4 linear olefins to be used as sources of isobutene have consequently become of extreme interest. In this respect, many catalysts are known for skeleton isomerization, among which alumina (U.S. Pat. No. 4436949, U.S. Pat. No. 4581474 and U.S. Pat. No. 4866211), halogenated alumina (U.S. Pat. No. 4654463, U.S. Pat. No. 4731490, U.S. Pat. No. 4778943, EP 54855, DE 3048693 and EP 71198) and silicized alumina (EP 66485, FR 2657605, DE 3340958, DE 3227676, U.S. Pat. No. 4010590, U.S. Pat. No. 4013589 and U.S. Pat. No. 4038337). To obtain operatively usable conversion values, with catalysts based on alumina, it is necessary to work at low space velocities. With such space velocity values secondary reactions of polymerization and cracking are present. These secondary reactions lower the selectivity of the process and cause the deactivation of the material which must be subjected to reaction cycles and regeneration and must therefore be stable also under the hydrothermal conditions which are created during the regeneration process.

U.S. Pat. No. 2422884 describes a process for the skeleton isomerization of linear olefins which uses as catalyst a suitably prepared alumina on the surface of which is deposited a quantity of boron oxide preferably of between $5 \times 10^{-4}$ and $8.6 \times 10^{-4}$ g per square meter of alumina. In this patent the optimum concentration of $B_2O_3$ is considered to be that which is sufficient to form a monomolecular layer of $B_2O_3$ on the surface of the alumina, i.e. a concentration of $6 \times 10^{-4}$ $gB_2O_3/m^2$.

SUMMARY OF THE INVENTION

It has now been surprisingly found that, by using a catalyst based on alumina containing much lower quantities of boron oxide than those necessary for creating a monolayer of $B_2O_3$ on the surface of the alumina, it is possible to perform the skeleton isomerization of linear olefins with a considerably higher-productivity to branched isomers than that which can be obtained with known catalysts based on alumina. In particular the catalysts used in our invention prove to be much more selective, with higher values of yield and productivity to branched isomers, than the preferred catalysts described in U.S. Pat. No. 2422884, and they are also stable in that, after numerous reaction-regeneration cycles, they show no loss of the $B_2O_3$ component. The present invention therefore relates to a process for the skeleton isomerization of linear olefins which consists in putting said olefins in contact with a catalyst comprising alumina on the surface of which is deposited boron oxide in a quantity which is lower than $2.1 \times 10^{-4} g/m^2$ of the surface of alumina.

DETAILED DESCRIPTION OF THE PREFERRED EMBODIMENTS

Figure 1:
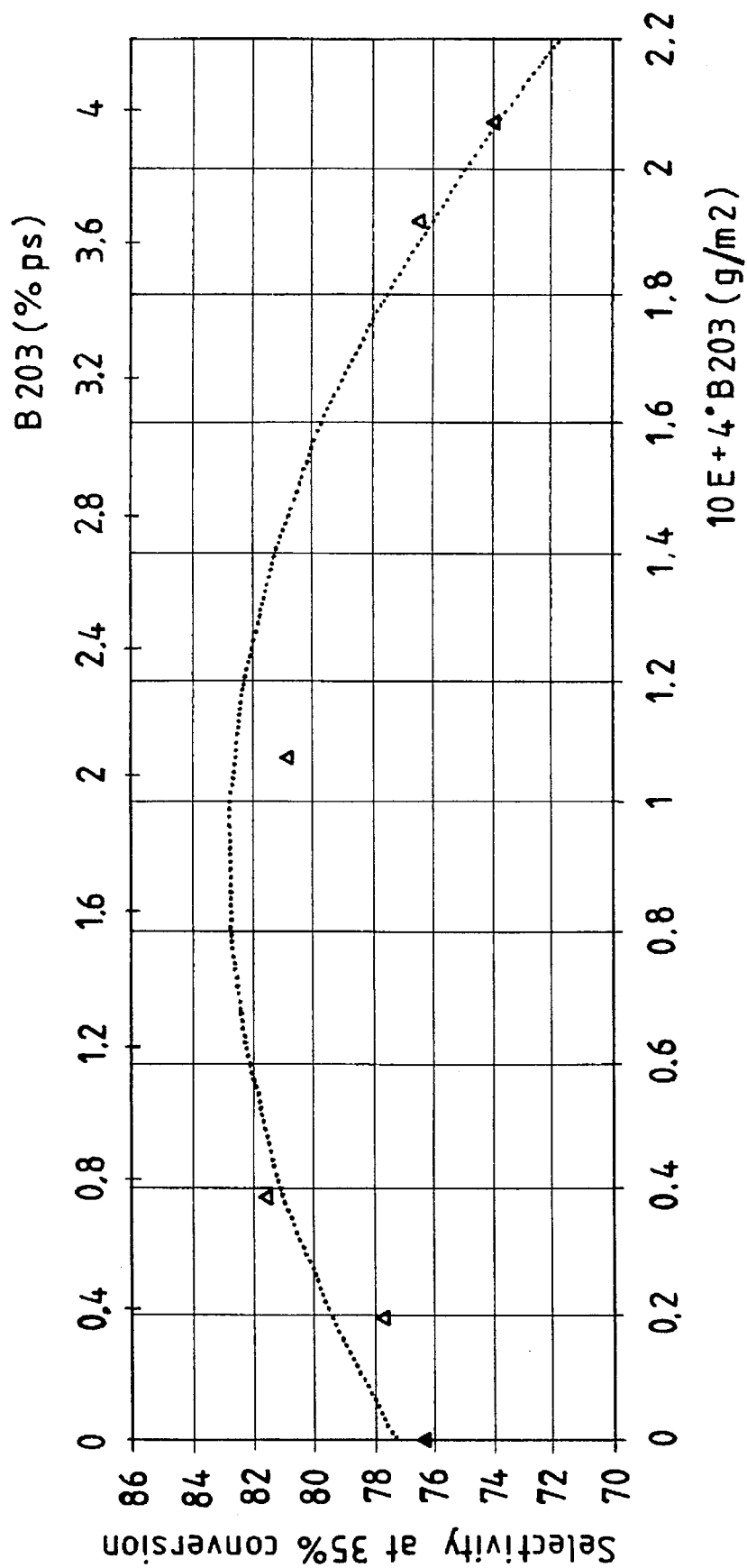
FIG. 1 shows the sel-$iC_4$ at 35% conversion as a function of $B_2O_3$ content in terms of % by weight (top) and $g/m^2 \times 10^4$ (bottom).

Aluminas which can be used in the present invention are preferably gamma-aluminas with a surface area of between 150 and 250 square meters per gram. The boron oxide present on the surface of the catalyst is preferably in a quantity of between $0.25 \times 10^{-4}$ and $1.5 \times 10^{-4}$ $g/m^2$ of the surface of the alumina. A preferred aspect of the present invention is that the quantity of boron oxide present on the surface of the catalyst is in a quantity which is greater than $0.25 \times 10^{-4}$ $g/m^2$ and lower than $1.5 \times 10^{-4}$ $g/m^2$ of the surface of alumina.

The catalysts of the present invention are prepared by treating the alumina with a boron compound and then subjecting it to controlled thermal treatments.

This boron compound can be an inorganic compound, such as ammonium tetraborate, boron oxide and, preferably, boric acid, or an organic compound of boron such as an alkyl ester of boric acid which can be represented with the general formula $B(OR)_3$ wherein R=Me, Et, iPr, nPr and nBu. Preferably R=Et, iPr.

The alumina is put in contact with an inorganic compound of boron dissolved in water or with an organic compound of boron, possibly dissolved in a solvent of the alcohol or hydrocarbon type, such as for example isopropyl alcohol or hexane. This operation can be carried out with different methods known in the art, such as for example impregnation to wettability, absorption by a solvent or deposition in the vapour phase when a boric ester is used operating without a solvent. When the operation is carried out in the organic phase the alumina is previously subjected to an activation procedure which eliminates the water absorbed, effected by means of thermal treatment carried out at 100°–300° C., or at room temperature under vacuum. The preparation procedure which involves the use of boric acid in an aqueous phase is preferable when an alumina containing alkali impurities, also in high quantities for example up to 0.3%, is used.

Once the boron compound has been put in contact with the alumina it binds itself to the surface. The reaction can be carried out at room temperature, or at a higher temperature which can reach the boiling point of the solvent selected. The contact time is between 30 minutes and 20 hours.

A catalyst precursor is thus obtained which is separated from the excess of the reactive and solvent, if present, by distillation or filtration. The catalyst is then obtained from the precursor by thermal treatment. This treatment consists in a decomposition phase of the precursor in an anhydrous or humid environment and a calcination phase in air at a temperature of about50°–100° C. higher than that to be used in the skeleton isomerization process.

The isomerization reaction is carried out by passing the flow of olefins to be isomerized on the catalyst at a temperature of between 400° and 500° C. and a pressure lower than 2 atm.

Linear olefins which can be well used for the process of the present invention are n-butenes and n-pentenes. The process is preferably carried out in the presence of water vapour. Quantities of vapour of less than 3% by weight with respect to the feed are, for example, suitable. When the feed consists of n-butenes, it is preferable to operate at a temperature of between 450° and 490° C., at a partial pressure of the olefins of less than 1 atm and a space velocity of the liquid (LHSV) of between 2 and 16, or even more preferably of between 4 and 11. The most favorable results of the isomerization of n-pentenes are obtained by operating preferably at a temperature of between 400° and 450° C., at a partial pressure of the olefins of less than 1 arm and a space velocity of the liquid of between 12 and 22.

EXAMPLES

EXAMPLE 1

Preparation of the catalyst 10 g of gamma-alumina in extruded form, with a surface area of about 200 $M^2/g$, a pore volume of 0.43 ml/g, poured density at a 20–25 mesh particle size equal to 0.62 g/ml, containing 24 ppm of Na, are activated in a nitrogen flow for 12 hours at 300° C. and cooled in an anhydrous environment.

The impregnating solution is then prepared by weighing 15.53 g of $B(iPrO)_3$ in a 25 ml flask and bringing it to volume with isopropanol. 6.6 ml of this solution are used to impregnate the alumina to wettability, and this is then left to react in a closed flask at 50° C. for 24 hours. At the end of the reaction the material is placed in a flow of anhydrous nitrogen, at a temperature which is brought to 200° C. in 2 hours and then kept at 200° C. for 5 hours to distill the solvent and $B(iPrO)_3$ which has not been bound to the alumina. The catalyst precursor thus obtained is subsequently subjected to hydrolytic decomposition treatment in a flow of humid nitrogen, at 200° C. for 17 hours. The calcination is then carried out by bringing the temperature at 50° C./hour to 550° C. and maintaining it at this value for 3 hours. The quantity of -$B_2O_3$, evaluated by chemical analysis, which is found to be charged onto the alumina is equal to 2.7% by weight, corresponding to $1.38\times10^{-4}$ g$B_2O_3/m^2$

EXAMPLE 2

Preparation of the catalyst 15 g of gamma-alumina in extruded form, as that used in example 1, are activated in muffle (static atmosphere) for 12 hours at 300° C. and cooled in an anhydrous environment.

3.03 g of $B(iPrO)_3$ and 18.9 g of n-hexane are mixed in a flask, the alumina is added and the mixture left in a closed flask at 25° C. for 6 hours. The solvent is separated by filtration, the mixture dried at 120° C. for 12 hours and the catalyst precursor is decomposed by calcination in a reactor in an air flow bringing the temperature to 550° C. in an hour and maintaining it at this value for another hour. The quantity of $B_2O_3$ which is charged on the alumina, evaluated by chemical analysis, is equal to 1.9% by weight, corresponding to $0.97\times10^{-4}$ g/$m^2$.

EXAMPLE 3

Preparation of the catalyst 20 g of gamma-alumina in extruded form, with a surface area of about 200 $m^2/g$, a pore volume of 0.72 ml/g, poured density at a 20–25 mesh particle size equal to 0.6 g/ml, containing 450 ppm of Na, are immersed in 40 ml of an aqueous solution containing 2 g of $H_3BO_3$ and left at 70° C. for about 16 hours. The solid is separated from the water by filtration, is washed on the filter, dried at 120° C. for 16 hours and calcinated at 550° C. for 3 hours. Upon chemical analysis the resulting content of $B_2O_3$ is 4% by weight, corresponding to $2.08\times10^{-4}$ g/$m^2$.

EXAMPLE 4

Preparation of the catalyst 20 g of gamma-alumina in extruded form, with a surface area of about 200 $m^2/g$, a pore volume of 0.48 ml/g, poured density at a 20–25 mesh particle size equal to 0.76 g/ml, containing 28 ppm of Na, are immersed in 40 ml of an aqueous solution containing 0.36 g of $H_3BO_3$ and left at 70° C. for about 23 hours. The solid is separated from the water by filtration. It is washed on the filter, dried at 120° C. for 16 hours and calcinated at 550° C. for 3 hours. Upon chemical analysis the resulting content of $B_2O_3$ is 0.4% by weight, corresponding to $0.20\times10^{-4}$ g/$m^2$.

EXAMPLE 5

Preparation of the catalyst

The same procedure is carried out as in example 4 with 20 g of alumina and 0.73 g of $H_3BO_3$. Upon chemical analysis the resulting content of $B_2O_3$ is 0.77% by weight, corresponding to $0.39\times10^{-4}$ g/$m^2$.

EXAMPLE 6

Preparation of the catalyst

The same procedure is carried out as in example 4 with 20 g of alumina and 1.03 g of $H_3BO_3$. Upon chemical analysis the resulting content of $B_2O_3$ is 2.1% by weight, corresponding to $1.08\times10^{-4}$ g/$m^2$.

EXAMPLE 7

Preparation of the catalyst

The same procedure is carried out as in example 4 with 20 g of alumina and 2.0 g of $H_3BO_3$, at 70° C. Upon chemical analysis the resulting content of $B_2O_3$ is 3.7% by weight, corresponding to $1.92\times10^{-4}$ g/$m^2$.

EXAMPLE 8

Preparation of catalyst

The same procedure is carried out as in example 4 with 20 g of alumina and 2.2 g of $H_3BO_3$. Upon chemical analysis the resulting content of $B_2O_3$ is 4.0% by weight, corresponding to $2.08\times10^{-4}$ g/$m^2$.

EXAMPLE 9

Preparation of the catalyst 20 g of gamma-alumina like that used in example 1, are immersed in 24.2 ml of an aqueous solution containing 1.10 g of $H_3BO_3$ and left at 50° C. for about 16 hours. The solid is separated from the water by filtration, it is washed on the filter, dried at 120° C. for 16 hours and calcinated at 550° C. for 3 hours. Upon chemical analysis the resulting content of $B_2O_3$ is 2% by weight, corresponding to $1.02\times10^{-4}$ g/$m^2$.

EXAMPLE 10

Preparation of the comparative catalyst 20 g of alumina of the type used in example 4 are immersed in 40 ml of an aqueous solution containing 33.3 mmoles of acetic acid and left in contact with the acid solution at 70° C. for 20 hours. At the end of the treatment

EXAMPLE 11

Preparation of catalyst 15 g of alumina in extruded form, of the type used in example 1, are activated in a reactor in a flow of anhydrous nitrogen for about 10 hours. The alumina is then rapidly cooled to a temperature of 80° C. and is subjected for 23 hours to a flow of 160–170 ml/min of anhydrous nitrogen which is bubbled at room temperature in B(iPrO)$_3$. At the end of the reaction the solid is subjected to a flow of dry nitrogen for 1 hour still at 80° C. and then calcinated in the reactor in a flow of air at up to 400° C. for 3 hours. Under these conditions 4.3 g of B(iPrO)$_3$ are put in contact with the alumina. Upon chemical analysis the resulting content of B$_2$O$_3$ is 1.78% by weight, corresponding to $0.90 \times 10^{-4}$ gB$_2$O$_3$/m$^2$.

EXAMPLE 12

Comparative catalyst

A comparative catalyst composed of silicized alumina is prepared according to FR 2657605. The silicized alumina described in FR 2657605 also contains palladium which does not influence the catalytic performance of the silicized alumina, but is introduced into the catalyst to facilitate the regeneration phase. The comparative catalyst of the present example was therefore prepared without palladium.

100 g of alumina of the type used in example 4 are activated in a muffle at 500° C. for 2 hours and cooled in an anhydrous environment. An impregnating solution is prepared by mixing 7.2 ml of tetraethylorthosilicate, 1.8 ml of water and 54.6 ml of pure ethyl alcohol. The alumina is impregnated to wettability and left for 6 hours at room temperature. The impregnated support is then placed in an oven at 40° C. in a humid atmosphere for 12 hours. The temperature is then raised in an hour to 95° C., still in a humid atmosphere, and these conditions are left for 12 hours. The catalyst is then dried in an anhydrous atmosphere at 110° C. for 12 hours and calcinated in air at 630° C.

EXAMPLE 13

Comparative catalyst 100 g of gamma alumina of the type used in example 3 are activated in a muffle at 200° C. for 12 hours and cooled in an anhydrous environment. 8.45 g of tetraethylsilicate are weighed in a flask and brought to 228 ml with n-hexane, the temperature is brought to 50° C., the alumina is added and the mixture left at 50° C. for 120 minutes. The liquid is separated by filtration and the following thermal treatments are carried out in a reactor: the mixture is brought in 1 hour to 180° C. in a flow of anhydrous nitrogen to distill the excess solvent and reactive, it is kept for 2 hours in a flow of saturated nitrogen with water at room temperature to hydrolytically decompose the silicon compound anchored to the surface. Calcination is then carried out in air for 3 hours at 550° C. Upon chemical analysis the resulting silicon content is equal to 2.4%.

EXAMPLE 14

Comparative catalyst

The same procedure is carried out as in example 11 at a temperature of 120° C. Upon chemical analysis the resulting content of B$_2$O$_3$ is 7.6% by weight, corresponding to $4.11 \times 10^{-4}$ g/m$^2$.

EXAMPLE 15

Comparative catalyst

A comparative catalyst composed of alumina borate is prepared according to U.S. Pat. No. 2422884. 20 g of alumina of the type used in example 4 are immersed in 50 ml of an aqueous solution containing 10.35 g of H$_3$BO$_3$ and left at reflux temperature for 18 hours. At the end of the treatment the support is separated from the solution by filtration, dried at 110° C. and calcinated at 550° C. for 6 hours. Upon chemical analysis the resulting content of B$_2$O$_3$ is 8.1% by weight, corresponding to $4.40 \times 10^{-4}$ g/m$^2$.

EXAMPLE 16

Catalytic test

The catalyst prepared in example 5, the alumina as such and the catalyst of example 12 are subjected to a catalytic test in the skeleton isomerization of a mixture of n-butenes.

The composition of this mixture, expressed as a percentage by weight, is shown in the following table:

| | |
|---|---|
| propylene | 0.001 |
| propane | 0.019 |
| iso-butane | 0.082 |
| n-butane | 0.124 |
| iso-butene (iC$_4$=) | 0.298 |
| 1-butene | 98.838 |
| 2-butene (trans) | 0.022 |
| 2-butene (cis) | 0.016 |
| H$_2$O | 0.600 |

A fixed-bed reactor is used, and 2 ml of catalyst with a 20–25 mesh particle size are charged. The feeding is passed over the catalyst at a temperature of 470° C., total pressure of 1 atmosphere, and LHSV of between 4 and 11.

The reaction discharge is condensed at the outlet of the reactor and subjected to gaschromatographic analysis.

The results obtained are shown in the following table A:

TABLE A

| | catalyst | | |
|---|---|---|---|
| | Al$_2$O$_3$/B$_2$O$_3$ (ex. 5) | Al$_2$O$_3$/SiO$_2$ (ex. 12) | Al$_2$O$_3$ |
| LHSV | 10.5 | 5 | 7 |
| T (°C.) | 470 | 470 | 470 |
| tos (min) | 30 | 30 | 30 |
| conv. (% wt) | 35.2 | 34.6 | 34.8 |
| sel iC4 = (% wt) | 81.7 | 80.0 | 75.3 |
| yield iC4 = (% wt) | 28.8 | 27.7 | 26.2 |
| prod iC4 = (Kg/l/hour) | 1.90 | 0.87 | 1.16 | wherein:

tos=time on stream conv=conversion of linear butenes calculated as:

(linear butenes at feed − linear butenes at exit) × 100/
(linear butenes at feed)
sel = selectivity to the indicated product, calculated as:
product at exit × 100/(linear butenes at feed −
linear butenes at exit)
iC4 = isobutene;
yield = yield of isobutene calculated as:
(conv × sel)/100
prod = productivity to isobutene in kilograms of
butenes per hour per litre of catalyst,
calculated as:
(yield × LHSV × density of butenes)/100
wherein density of butenes = 0.6 Kg/l It is evident from the results that the catalyst of the present invention has a higher productivity to isobutene, with higher values of selectivity, compared to both the alumina and the silicized alumina prepared as described in the known art.

EXAMPLE 17

Catalytic test

The catalyst prepared in example 3, the catalyst of example 13 and the alumina support as such used for both preparations are subjected to a catalytic test in the skeleton isomerization of a mixture of n-butenes. The composition of this mixture, expressed as a percentage by weight, is the same as that used in example 16. A fixed-bed reactor is used, and 2 ml of catalyst with a 20–25 mesh particle size are charged. The feeding is passed over the catalyst at 470° C., atmospheric pressure and LHSV of between 4 and 10. An on line analysis is made of the reaction discharge, maintaining the transfer line which connects the reactor to the gas chromatograph at about 250° C. The results obtained are shown in table B below:

TABLE B

| | catalyst | | |
|---|---|---|---|
| | $Al_2O_3/B_2O_3$ (ex. 3) | $Al_2O_3/SiO_2$ (ex. 13) | $Al_2O_3$ |
| LHSV | 9.40 | 4.30 | 4.10 |
| T (°C.) | 470 | 470 | 470 |
| tos (min) | 30 | 70 | 70 |
| conv. (% wt) | 34.9 | 34.4 | 25.3 |
| sel iC4 = (% wt) | 79.1 | 79.0 | 76.7 |
| sel C1–C3 (% wt) | 3.1 | 4.1 | 5.5 |
| sel C4sat (% wt) | 0.6 | 0.4 | 0.9 |
| sel C5 (% wt) | 6.7 | 9.3 | 10.4 |
| sel C5+ (% wt) | 10.5 | 7.2 | 6.5 |
| yield iC4 = (% wt) | 27.6 | 27.2 | 19.4 |
| prod iC4 = (Kg/l/hour) | 1.55 | 0.70 | 0.48 | wherein:

C1–C3 hydrocarbons with from 1 to 3 carbon atoms; C4sat paraffins with 4 carbon atoms; C5 hydrocarbons with 5 carbon atoms; C5+ hydrocarbons with more than 5 carbon atoms.

It is evident from the results that the catalyst used in the present invention has a definitely higher productivity to isobutene, with higher selectivity values compared to both the alumina as such and a catalyst of the group of silicized aluminas.

EXAMPLE 18

Catalytic test

The catalysts with an increasing amount of $B_2O_3$, described in examples 4–8, were compared in a skeleton isomerization test carried out feeding a charge having the composition indicated in example 16, at a temperature of 470° C., at atmospheric pressure, and with an on line analysis of the reaction discharge after about 30 minutes of tos. The results obtained are shown in table C:

TABLE C

| catal. | $B_2O_3$ (g/m²) | LHSV | conv (% wt) | sel iC4 = (% wt) |
|---|---|---|---|---|
| ex. 4 | $0.2 \times 10^{-4}$ | 7.5 | 38.2 | 76.3 |
| | | 10.5 | 31.6 | 80.6 |
| ex. 5 | $0.39 \times 10^{-4}$ | 7.5 | 40.3 | 77.6 |
| | | 9.0 | 38.0 | 79.4 |

TABLE C-continued

| catal. | $B_2O_3$ (g/m²) | LHSV | conv (% wt) | sel iC4 = (% wt) |
|---|---|---|---|---|
| | | 10.5 | 35.2 | 81.7 |
| ex. 6 | $1.08 \times 10^{-4}$ | 7.5 | 40.4 | 77.0 |
| | | 9.0 | 37.6 | 79.2 |
| | | 10.5 | 35.6 | 80.6 |
| ex. 7 | $1.92 \times 10^{-4}$ | 7.5 | 39.8 | 73.0 |
| | | 9.0 | 36.8 | 75.1 |
| | | 10.5 | 34.6 | 76.4 |
| ex. 8 | $2.08 \times 10^{-4}$ | 7.5 | 39.9 | 70.5 |
| | | 9.0 | 37.2 | 72.3 |

FIG. 1 shows the selectivity values, measured at 35% conversion, in relation to the content of $B_2O_3$ of the different preparations. It is evident that, with the same conversion, the best selectivity results are obtained within a range of between $0.25 \times 10^{-4}$ and $1.5 \times 10^{-4}$ g$B_2O_3$/m² of alumina.

EXAMPLE 19

Catalytic test

The catalysts of the present invention described in examples 5 and 9 were compared with the catalyst of example 15 and the catalyst of example 14. The skeleton isomerization test was carried out feeding a charge having the composition indicated in example 16, at a temperature of 470° C., at atmospheric pressure, and with an on line analysis of the reaction discharge after about 30 minutes of tos. The results obtained are shown in tables D and E below:

TABLE D

| catal. | LHSV | conv. (% wt) | sel iC4 = (% wt) |
|---|---|---|---|
| ex. 5 | 4.4 | 48.5 | 68.0 |
| ex. 9 | 4.2 | 48.8 | 64.7 |
| ex. 14 | 7.0 | 48.9 | 44.0 |
| ex. 15 | 9.0 | 48.6 | 36.9 |

TABLE E

| catal. | LHSV | conv. (% wt) | sel iC4 = (% wt) |
|---|---|---|---|
| ex. 5 | 9.1 | 38.0 | 79.4 |
| ex. 9 | 9.1 | 37.6 | 79.2 |
| ex. 14 | 8.8 | 48.0 | 45.0 |
| ex. 15 | 9.0 | 48.6 | 36.9 |

These results clearly show the high selectivity to isobutene which can be obtained with the catalysts used in the present invention, both when the selectivity values at isoconversion and the selectivity at equal LHSV are compared.

Catalysts with a higher content of boron as described in the known art give a much lower performance and cannot be used for industrial purposes.

EXAMPLE 20

Stability test

The catalyst described in example 1 (content of $B_2O_3$= 2.7%) was subjected to hydrothermal treatment consisting in fluxing the catalyst in a reactor at a temperature of 570° C. with a flow of saturated nitrogen with water at room temperature, a pressure of 1 atmosphere and GHSV=1500 for 800 hours. After this treatment upon chemical analysis the resulting content of $B_2O_3$ was 2.7.

This test shows that the catalysts used in the present invention are stable in the hydrothermal environment which is produced in the regeneration phase in that there proves to be no loss of the component $B_2O_3$.

EXAMPLE 21

Decay test

The catalyst prepared in example 5 was subjected to the isomerization catalytic test in a fixed-bed reactor, charging 2 ml of catalyst with a 20–25 mesh particle size.

The test is carried out at 480° C., a total pressure of 1 arm, LHSV=8, feeding a charge having the following composition expressed as percentage by weight:

| | |
|---|---|
| ethylene | 0.003 |
| propylene | 0.009 |
| isobutane | 50.549 |
| butene-1 | 48.819 |
| n-butane | 0.021 |
| butene-2trans | 0.001 |
| butene-2cis | 0.002 |
| water | 0.596 |

The reaction discharge is condensed at the outlet of the reactor and subjected to gaschromatographic analysis. The results are shown in table F below:

TABLE F

| tos (hours) | conv (% wt) | sel iC4 = (% wt) | yield iC4 = (% wt) | prod iC4 = (Kg/l/hour) |
|---|---|---|---|---|
| 0.50 | 41.6 | 78.9 | 32.82 | 0.63 |
| 3.00 | 40.3 | 80.3 | 32.36 | 0.62 |
| 8.00 | 37.4 | 81.6 | 30.52 | 0.59 |

The results show that the decline of the catalytic activity in about 8 hours of reaction is moderate.

EXAMPLE 22

Catalytic test

The activity of the catalyst prepared in example 5 is compared to that of the support as such and that of the alumina treated as described in example 10. The skeleton isomerization catalytic test of linear butenes, whose composition is shown in example 16, was carried out at 470° C. and atmospheric pressure. There was total collection of the reaction discharge which was condensed at the outlet of the reactor in a trap cooled with dry ice. The collection was centered at about 30 minutes of tos.

The results obtained are shown in table G below:

TABLE G

| catalyst | LHSV | conv. (% wt) | sel iC4 = (% wt) |
|---|---|---|---|
| $Al_2O_3$ | 4.41 | 39.0 | 70.0 |
| $Al_2O_3$ (ex. 10) | 4.55 | 38.8 | 69.7 |
| $Al_2O_3/B_2O_3$ (ex. 5) | 4.41 | 48.5 | 68.0 |
| | 7.5 | 40.3 | 77.6 |

The results show that the catalyst used in the present invention has a higher conversion than alumina as such and alumina washed in acid, and in addition with equal conversion it also has a much higher selectivity to branched products.

EXAMPLE 23

Stability test

The catalyst of example 8 was subjected to hydrothermal treatment consisting in fluxing the catalyst in a reactor with a flow of saturated air with water at room temperature, at a temperature of 570° C., atmospheric pressure and GHSV= 1500, for more than 1200 hours, occasionally controlling the catalytic activity by means of a skeleton isomerization test.

The isomerization test was carried out at 470° C., with LHSV=4.4, at atmospheric pressure and feeding a mixture of butenes whose composition is shown in example 16. On line analyses of the reaction discharge were carried out at about 30 minutes of tos.

The results are shown in table H below:

TABLE H

| Hydrothermal treatment | | | | | |
|---|---|---|---|---|---|
| duration (hours) | 2.5 | 90.0 | 255.0 | 432.0 | 1170.0 |
| conversion (% wt) | 44.4 | 44.5 | 44.6 | 44.4 | 44.6 |
| sel iC4 = (% wt) | 67.2 | 66.5 | 67.1 | 67.6 | 67.2 |

EXAMPLE 24

Catalytic test

The catalyst of example 1 was subjected to a skeleton isomerization catalytic test of pentene-1.

A fixed-bed reactor was used charging 1 ml of catalyst at 20–25 mesh. The feeding, composed of pure 1-pentene (C5 lin), is passed over the catalyst at 430° C., atmospheric pressure and LHSV=18. The product is totally collected by cooling and subjected to gaschromatographic analysis. The results obtained are shown in table I below:

TABLE I

| tos (hours) | C5lin (% wt) | conv (% wt) | sel iC5 = (% wt) | yield iC5 = (% wt) | prod iC5 = (Kg/l/ hour) |
|---|---|---|---|---|---|
| 0.5 | 100 | 59.7 | 92.0 | 54.9 | 6.3 |
| 5.5 | | 51.2 | 93.0 | 48.1 | 5.5 |
| 28.0 | | 30.3 | 94.0 | 28.5 | 3.2 | wherein:

C5 lin is the percentage by weight of the linear pentenes present in the feeding;

prod iC5=is the productivity in Kg of branched pentenes per hour per liter of catalyst, calculated as (yield× LHSV×density)/100, wherein the density is 0.4 Kg/l.

EXAMPLE 25

A catalyst with a content of $B_2O_3$ equal to $1.54 \times 10^{-4} g/m^2$, prepared in accordance with example 4 using 1.51 g of $H_3BO_3$, was subjected to a skeleton isomerization catalytic test of pentene-1 like the one described in example 24, carried out at 420° C.

The results obtained are shown in table L below:

TABLE L

| tos (hours) | C5lin (% wt) | conv (% wt) | sel iC5= (% wt) | yield iC5= (% wt) | prod iC5= (Kg/l/h) |
|---|---|---|---|---|---|
| 0.5 | 100 | 54.2 | 90.2 | 48.90 | 5.63 |
| 2.5 |  | 49.6 | 92.3 | 45.80 | 5.27 |
| 4.0 |  | 45.2 | 92.9 | 42.00 | 4.83 |

EXAMPLE 26

Table M below shows the data relating to conversion, selectivity and productivity which can be calculated from the yield data contained in examples 27, 28 and 31 of U.S. Pat. No. 2422884:

TABLE M

| ex. No. | 27 | 28 | 31 |
|---|---|---|---|
| $B_2O_3$ (g/m$^2$) | $3.26 \times 10^{-4}$ | $3.26 \times 10^{-4}$ | $4.01 \times 10^{-4}$ |
| T (°C.) | 500 | 500 | 500 |
| LHSV | 4 | 3 | 3 |
| C5lin (% wt) | 96 | 96 | 91 |
| conv (% wt) | 75.5 | 69.2 | 79.6 |
| sel iC5 = (% wt) | 48.6 | 70.2 | 35.3 |
| yield iC5 = (% wt) | 36.8 | 48.6 | 28.1 |
| prod iC5 = (Kg/l/hour) | 0.94 | 0.93 | 0.54 |

These results show how the catalysts described in U.S. Pat. No. 2,422,884 with a higher content of boron give a much lower performance than those obtained with the present invention.

We claim:

1. A process for the skeleton isomerization of a linear olefin which comprises contacting said olefin under isomerization conditions with a catalyst comprising a gamma-alumina on the surface of which boron oxide is deposited in a quantity lower than $2.1 \times 10^{-4}$ g/m$^2$ of the surface of the alumina.

2. The process of claim 1, wherein said boron oxide is present in a quantity of from $0.25 \times 10^{-4}$ to $1.50 \times 10^{-4}$ g/m$^2$.

3. The process of claim 2, wherein said boron oxide is present in a quantity higher than $0.25 \times 10^{-4}$ and lower than $1.50 \times 10^{-4}$ g/m$^2$.

4. The process of claim 1, wherein said olefin is selected from the group consisting of n-butenes and n-pentenes.

5. The process of claim 1, wherein said contacting is carried out at a temperature of between 400° and 500° C. and at a pressure lower than 2 atm.

6. The process of claim 5, wherein said contacting is carried out in the presence of water vapor.

7. The process of claim 5, wherein said olefin is n-butenes and said contacting is carried out at a temperature of between 450° and 490° C., at a partial pressure of said olefin which is lower than 1 arm and a space velocity of the liquid (LHSV) of between 2 and 16.

8. The process of claim 7, wherein said space velocity of the liquid (LHSV) is between 4 and 11.

9. The process of claim 5, wherein said olefin is n-pentenes and said contacting is carried out at a temperature of between 400° and 450°, at a partial pressure of said olefin which is lower than 1 atm and at a space velocity of the liquid of between 12 and 22.

* * * * *